United States Patent
Kikuchi et al.

(10) Patent No.: US 7,297,690 B2
(45) Date of Patent: Nov. 20, 2007

(54) FLUORESCENT LANTHADINE COMPLEX

(75) Inventors: Kazuya Kikuchi, Kanagawa (JP); Shinya Iwasawa, Tokyo (JP); Tetsuo Nagano, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 123 days.

(21) Appl. No.: 10/536,382

(22) PCT Filed: Feb. 17, 2004

(86) PCT No.: PCT/JP2004/001680

§ 371 (c)(1), (2), (4) Date: Jan. 9, 2006

(87) PCT Pub. No.: WO2004/074254

PCT Pub. Date: Sep. 2, 2004

(65) Prior Publication Data

US 2006/0149043 A1 Jul. 6, 2006

(30) Foreign Application Priority Data

Feb. 24, 2003 (JP) .............................. 2003-045786

(51) Int. Cl.
C07F 7/00 (2006.01)
C07F 9/00 (2006.01)

(52) U.S. Cl. ...................................................... 514/185
(58) Field of Classification Search ................ 514/185; 546/7, 9, 19

See application file for complete search history.

(56) References Cited

U.S. PATENT DOCUMENTS 2,616,855 A 11/1952 Wheelock
6,277,841 B1 8/2001 Rajagopalan et al.

OTHER PUBLICATIONS

Zaharevitz, et al., "Discovery of novel HIV-1 reverse transcriptase inhibitors . . . ", Medicinal Chemistry Research 1999 vol. 9 (7/8) p. 551-564.

Primary Examiner—Michael G. Hartley
Assistant Examiner—Jagadishwar Samala
(74) Attorney, Agent, or Firm—Gary C Cohn PLLC

(57) ABSTRACT

A luminescent lanthanide complex using a photo induced electron transfer as the luminescence controlling principle is presented. The complex comprises a substituted 2-quinolinol containing a sensor group and a complex group and lanthanide ion ($Ln^{3+}$). This complex is allowed to be co-present in a liquid phase with a material to be measured, and the luminescence of said complex is measured.

11 Claims, 8 Drawing Sheets

1)

2)

3)

4)

FLUORESCENT LANTHADINE COMPLEX

TECHNICAL FIELD

The present invention relates to a novel complex comprising a substituted 2quinolinol and a lanthanide ion, more specifically, to a novel long-life luminescent complex comprising a substituted 2-quinolinol and a lanthanide ion, the luminescence intensity of which can be controlled using a photo-induced electron transfer (PET).

PRIOR ART

Luminescent lanthanide complexes are known to have luminescent characteristics starkly different from those of ordinary luminescent organic compounds and have long life luminescence, sharp luminescence spectra and large Stokes shifts. (Richardson, F. S.; Chemistry Review, 1982, 82, 541-552; Ginya Adachi "Rare Earth Story, Magicians Among Leading Edge Materials," Sangyo Tosho; Ginya Adachi "Rare Earth Chemistry," Kagaku Dojin.) By utilizing the characteristics of this luminescence and measuring the luminescence using a time resolved measurement, the luminescence emitted solely by a lanthanide complex can uniquely be detected upon eliminating the luminescence from other organic compounds having short luminescence lifetime. This approach allows the background noise to be suppressed, and highly sensitive detection having a greater S/N ratio than that of a luminescence detection system based on the luminescence of an ordinary organic compound becomes possible. A variety of luminescent lanthanide complexes have been developed previously as labeling reagents and were used in time resolved immunoassays and time resolved DNA hybridizations, and an increase in detection sensitivities has been reported. (Morton, R. C., et al. Anal. Chem. 1990, 62, 1841; Seveus, L. et al., Microsc. Res. Tech. 1994, 28, 149; Mathis, G. Clin. Chem. 1993, 39, 1953-1959.) A probe capable of detecting a target analytical material with high sensitivity can be developed by using the luminescence of the luminescent lanthanide complex having the characteristics mentioned above.

Recently an attempt was made to utilize a luminescent lanthanide complex itself as a sensor, and lanthanide complexes that change their luminescence characteristics depending upon the presence or absence of a target analytical material are being developed. (DeSilva, A. P. et al., Chem. Rev. 1997, 97, 1515; Bissell, R. A. et al. "In Luminescent Chemosensors for Ion and Molecule Recognition"; Garnik, A. W., Ed.; ACS Symposium Series 538; American Chemical Society; Washington, D.C., 1993; Chapter 4.) The main luminescence controlling methods involve either a change in the number of water ligands on lanthanide or a change in the chromophore itself.

Up to now, many luminescent probes have been developed in ordinary organic compounds, in which photo induced electron transfer has been used to control luminescence. The photo induced electron transfer principle is widely accepted as the mechanism for luminescence quenching and is caused by the transfer of electrons from electron donating locations to luminescent dye locations. If the luminescence from a luminescent lanthanide complex can be controlled using photo induced electron transfer, a probe capable of high sensitivity detection can be designed and developed using photo induced electron transfer as the luminescence controlling principle.

Several attempts to control the luminescence from lanthanide complexes such as the one shown by the formula below (chemical formula 4) using photo induced electron transfer have been reported. (Chem. Comm. 2000, 473-474; Chem. Comm. 1997, 1891-1892.)

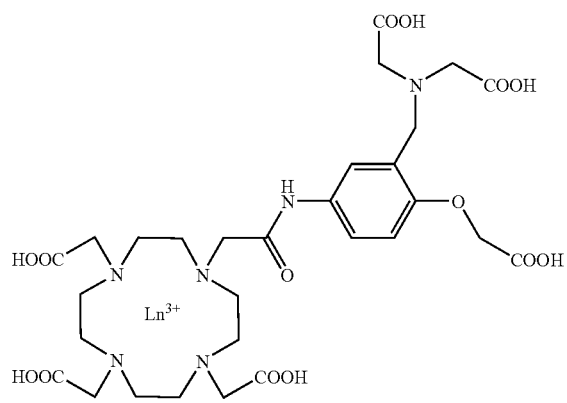

-continued

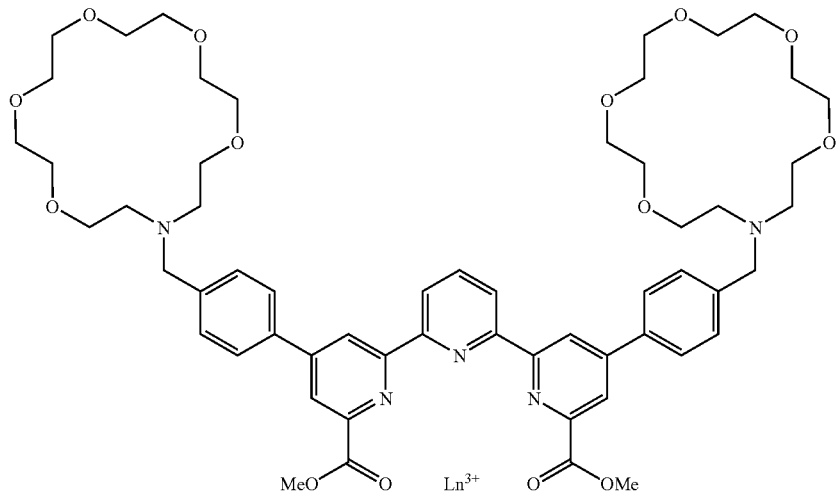

Problems to be Solved by the Invention

However, the previously reported lanthanide complexes that exhibit luminescence controlled using photo induced electron transfer (PET) do not have adequate quenching mechanisms and not enough change in luminescence could be achieved due to large levels of background luminescence. In addition, the lanthanide complexes emitted luminescence only in organic solvents due to inadequate coordination of the complexes on a lanthanide metal. By overcoming the deficiency, a probe based on a luminescent lanthanide complex having practical applications in many actual systems can be developed.

The objective of the present invention is to present a luminescent lanthanide complex utilizing photo induced electron transfer as the luminescence controlling principle. This complex needs to form a stable complex with lanthanide in water and to function in water. In addition, this complex must be completely controllable and emit no luminescence at all when quenched.

Means to Solve the Problems

The inventors discovered that the problems described above were solved by a complex comprising a lanthanide ion and a substituted 2-quinolinol containing a sensor group and a complex group, and the present invention was completed.

That is, the present invention is a luminescent lanthanide complex comprising a lanthanide and a substituted 2-quinolinol having a sensor group and a complex group on any two of the positions 3-8 in the 2-quinolinol represented by the formula below (chemical formula 1)

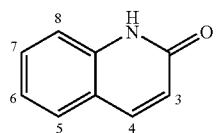

wherein the sensor group is represented by the formula below

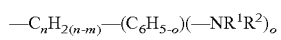

(wherein n is an integer of 1-5, m is an integer of 0-2 and smaller than n-1, o is 1 or 2, $R^1$ represents H, alkyl, —COX (wherein X represents alkyl or peptide) or —$CH_2CH_2$(NYCH$_2$CH$_2$)$_p$NY$_2$ (wherein Y independently represents H, alkyl or a group having the formula below (chemical formula 2)

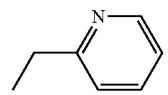

and p represents an integer of 0-3), and $R^2$ represents H or alkyl), and said lanthanide ion is complex bonded to said complex group, and the molar ratio of said substituted 2-quinolinol: said lanthanide is 1:0.9 to 1.1. The lanthanide means any one of the elements of $^{58}$Ce to $^{71}$Lu.

The complex group is derived from any one of the chelates (chemical formula 3) shown below

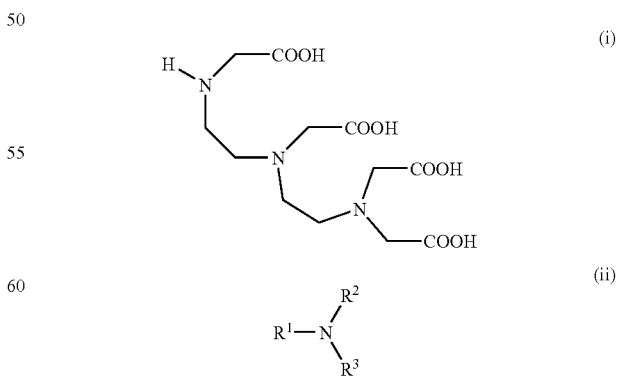

$R_1$ = H, $R_2$ = $R_3$ = $CH_2COOH$, IDA
$R_1$ = $CH_3$, $R_2$ = $R_3$ = $CH_2COOH$, MIDA
$R_1$ = $R_2$ = $R_3$ = $CH_2COOH$, NTA

-continued
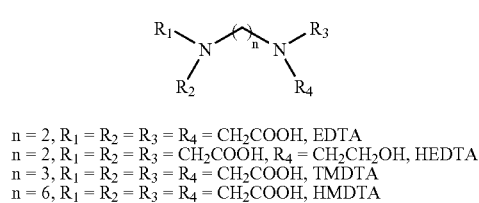
n = 2, R$_1$ = R$_2$ = R$_3$ = R$_4$ = CH$_2$COOH, EDTA
n = 2, R$_1$ = R$_2$ = R$_3$ = CH$_2$COOH, R$_4$ = CH$_2$CH$_2$OH, HEDTA
n = 3, R$_1$ = R$_2$ = R$_3$ = R$_4$ = CH$_2$COOH, TMDTA
n = 6, R$_1$ = R$_2$ = R$_3$ = R$_4$ = CH$_2$COOH, HMDTA
(iv)
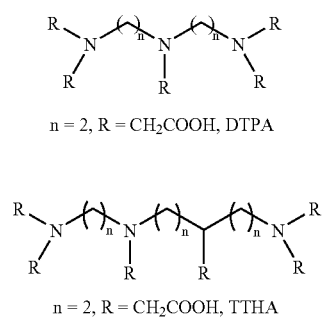
n = 2, R = CH$_2$COOH, DTPA
(v)
n = 2, R = CH$_2$COOH, TTHA
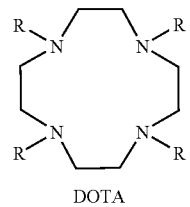
DOTA
(vi)
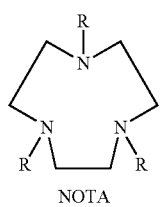
NOTA
(vii)
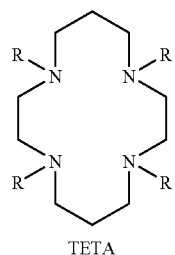
TETA
(viii)
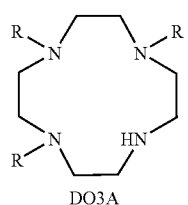
DO3A
(ix)
-continued
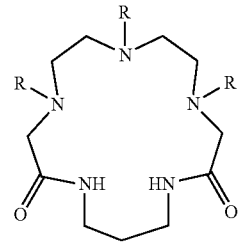
(x)
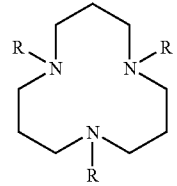
(xi)
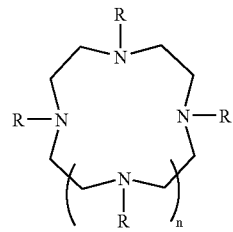
(xii)
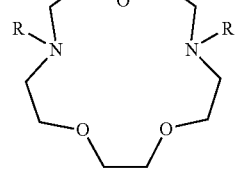
(xiii)
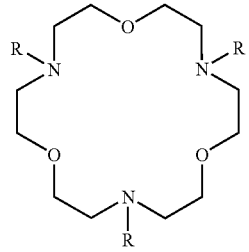
(xiv)
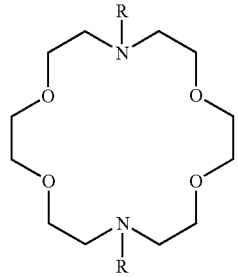
(xv)
R = CH$_2$COOH ((vi)~(xv))

(in the formula, IDA indicates iminodiacetic acid, MIDA indicates methyliminodiacetic acid, NTA indicates nitrilotriacetic acid, EDTA indicates ethylenediamine tetraacetic acid, HEDTA indicates 2-hydroxyethyl ethylene diamine tetraacetic acid, HMDTA indicates hexamethylenediamine tetraacetic acid, DTPA indicates diethylenetrinitilopentaacetic acid, TTHA indicates triethylenehexanitilopentaacetic acid, DOTA indicates 1,4,7,10-tetraazacyclododecane-1,4,7,10-tetraacetic acid and NOTA indicates 1,4,7-azacyclononane-1,4,7-triacetic acid) and one of the N atoms in the chelate is preferably bonded to said 2-quinolinol through —$CH_2(CONH)_q$— (wherein q represents 0 or 1, preferably 1).

As the chelate, (iv) DTPA and (vi) DOTA are preferred.

An amino group is added using a known method to positions 7, 3 or 4 of 2-quinolinol, and a chelate containing a carboxylic acid can form an amide linkage through the amino group to bond the chelate to 2-quinolinol.

A substitution location for the sensor groups and complex groups is preferably at positions 7, 4 or 3 in the 2-quinolinol. Furthermore, the positions 7, 4 and 3 are preferred in this order as the substitution sites for the sensor groups and complex groups in the 2-quinolinol, and the positions 4, 3 and 7 are preferred in this order as the substitution sites for the sensor groups in the 2-quinolinol. In addition, it is preferred that the complex group is bonded to position 7 of said 2-quinolinol while said sensor group is bonded to position 4 or 3 of said 2-quinolinol, or said complex group is bonded to position 4 of said 2-quinolinol while said sensor group is bonded to position 3 or 7 of said 2-quinolinol, or said complex group is bonded to position 3 of said 2-quinolinol while said sensor group is bonded to position 4 or 7 of said 2-quinolinol.

Furthermore, it is preferred that, in the sensor group, at least one amino group (—$NR^1R^2$) is positioned para to a divalent hydrocarbon group (—$C_nH_{2(n-m)}$—) on the benzene ring ($C_6H_{5-o}$), and the alkyl is methyl. It is more preferred that n is 1 and m is 0.

A complex of the present invention commonly can be prepared by mixing about equal amounts of a substituted 2-quinolinol and lanthanide in a polar solvent such as acetinitrile, methanol, water and the like and agitating them for about an hour or by heating and allowing them to reflux for about one to twelve hours.

Furthermore, the present invention is a method to measure the nature of a sample comprising allowing any one of the above luminescent lanthanide complex to be co-present in a liquid phase with said sample and measuring the luminescence of the complex.

As the solvent, polar solvents such as dimethyl sulfoxide, acetonitrile, methanol and the like is preferred and water is more preferred. The concentration of the complex, in the solvent, is preferably 0.1 nM to 0.1 mM and the concentration of a sample to be measured is preferably 0.1 nM to 0.2 mM.

For example, when a complex of the present invention is used with a hydrolase enzyme and the like as a sample to be measured, the sensor segment of the complex is decomposed by the sample to be measured resulting in a change in the luminescence intensity of the complex. Alternately, the sensor segment of a complex of the present invention is covalently bonded with $Ca^{2+}$, $Zn^{2+}$ or $H^+$ resulting in a change in the luminescence intensity of the complex. Also alternately, the sensor segment of a complex of the present invention undergoes a chemical reaction with NO or singlet oxygen with a subsequent change in the luminescence intensity of the complex. Therefore, a complex of the present invention functions as a probe for these samples to be measured.

EMBODIMENT OF THE INVENTION

Figure 1:
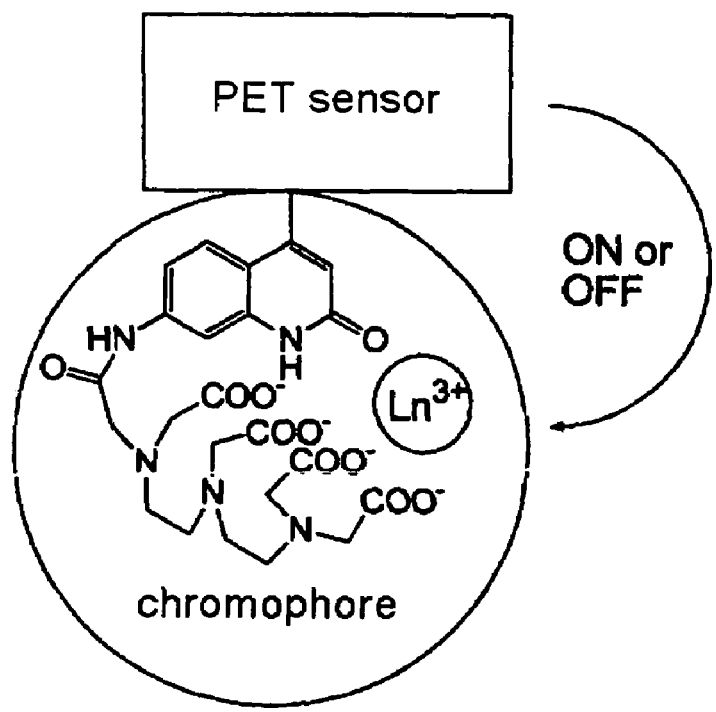
FIG. 1 shows the constitution of a complex of the present invention.

A complex of the present invention, as shown in FIG. 1, comprises a sensor section composed of sensor substituents and a chromophore section composed of a substituted 2-quinolinol, containing a complex group, and a lanthanide.

This complex is allowed to co-exist with a sample to be measured in a liquid phase, particularly in water. When the sample reacts with the amino groups in the sensor section, a change in the luminescence of this complex occurs. By observing the change, the nature of the sample can be characterized.

Figure 2:
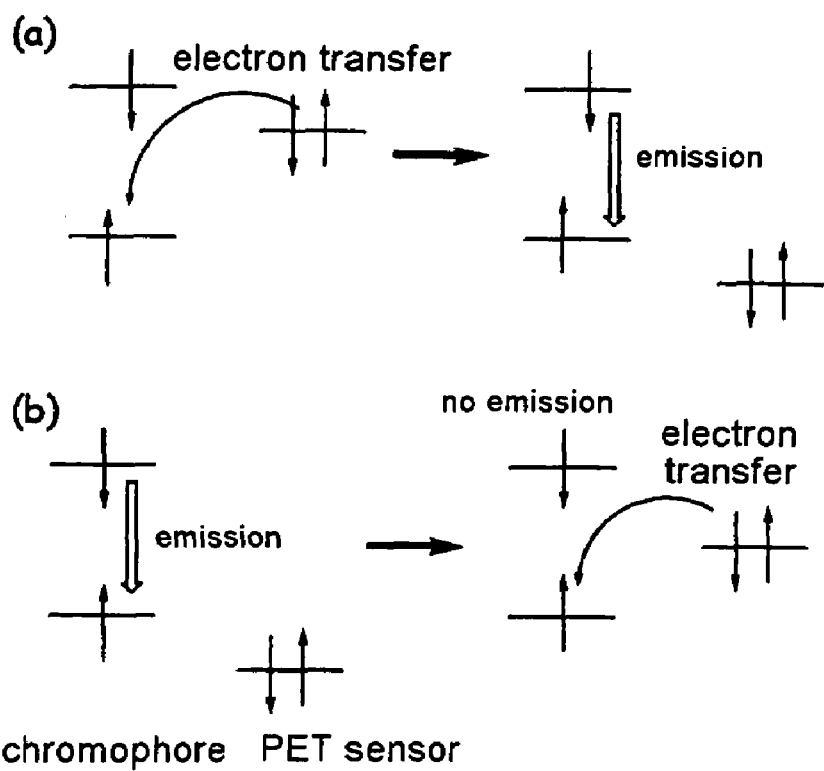
FIG. 2 shows the principle of the sensor function of a complex of the present invention. (a) shows a case wherein the electron donating nature of a sensor section is high, and (b) shows a case wherein the electron donating nature of a sensor is low.

For example, when the electron donating nature of the amino group is high (for example, when the sensor section is aniline), no luminescence is emitted from a chromophore as shown on the left of FIG. 2(a). When such a reaction induces a change in the amino group to a group having low electron donating nature (for example, into acetanilide), luminescence is emitted by the chromophore as shown on the right of FIG. 2(a). In a reverse situation, luminescence is quenched according to the reaction with a sample as shown in FIG. 2(b). By studying such luminescence, one can find an interaction between the complex of the present invention and the target sample. (Refer to DeSilva, A. P. et al., 1997, 97, 1515 for information on such a PET sensor principle.)

Figure 3:
FIG. 3 shows a reaction mechanism example of a complex of the present invention. (1) shows an example wherein a reaction group that reacts with a hydrolase enzyme such as caspase is incorporated into the PET sensor section; (2) shows an example wherein a reaction group that forms a coordinate bond with a zinc ion is incorporated into the PET sensor section; (3) shows an example wherein a reaction group that adds a hydrogen ion is incorporated into the PET sensor section; (4) shows an example wherein a reaction group that reacts with nitrogen monoxide is incorporated into the PET sensor section.
Figure 3:
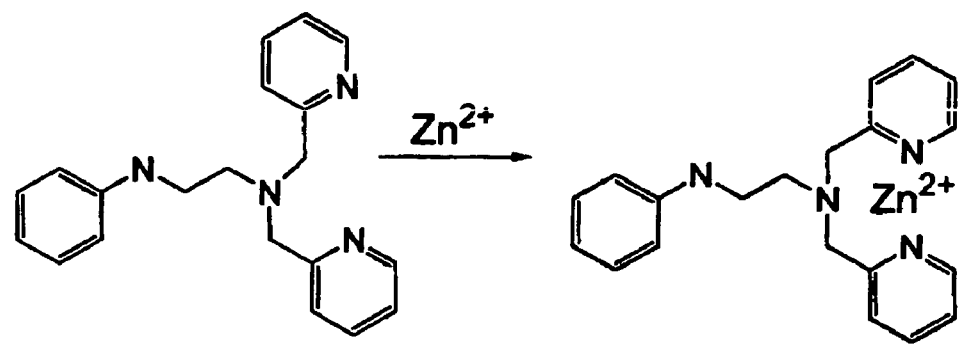
Figure 3:
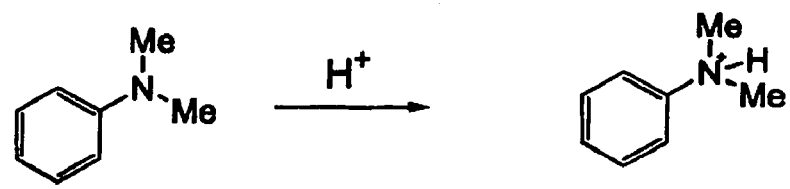
Figure 3:
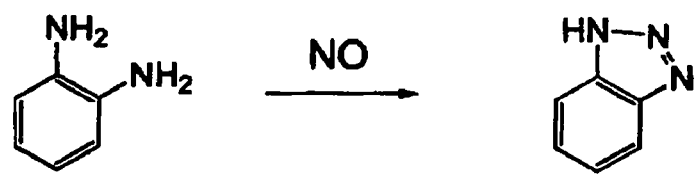

Based on such a principle, some examples can be shown below as examples in which a complex of the present invention is utilized as a probe. However, the applications are not restricted to the examples. The reaction mechanisms involved in each example are shown in FIG. 3.

(1) A reaction group (a peptide: DEVD) capable of reacting with a hydrolase enzyme such as caspase is incorporated into a PET sensor.

This enables that the hydrolase enzymes such as caspase and the like can be specifically detected. The intra-cellular formation of a hydrolase such as caspase can be visualized. This application is very effective in analyzing the mechanisms of life related phenomena such as apoptosis. The tool can be applied to measuring the activity of a hydrolase such as caspase and can also be applied to the high throughput screening of interfering agents for a hydrolase such as caspase.

No example of an application to a conventional organic luminescence probe has been published, but a complex of the present invention is an application target since it can definitely induce a change in luminescence intensity.

(2) A reaction group forming a coordinate bond to a zinc ion is incorporated into the PET sensor section.

This example makes the unique detection of $Zn^{2+}$ possible. The intra-cellular formation of $Zn^{2+}$ can be visualized. An example in which the $Zn^{2+}$ measurements are applied to an organic luminescence probe has been published. (Hirano, T., et al., J. Am. Chem. Soc., 2000, 122, 12399.)

(3) A reaction group containing added hydrogen ions is incorporated into a PET sensor section.

Changes in pH can be measured using intensity changes in long life luminescence. An example in which measurements of changes in pH are applied to an organic luminescent probe has been published. (Sellinger, B. K, Aust. J. Chem. 1977, 30, 2087.)

(4) A reaction group containing nitrogen monoxide is incorporated into a PET sensor section.

Unique detection of NO is possible. Intracellular NO formation can be visualized. Such an example can be applied to measure the activation of NO synthetase and can also be applied to high throughput screening of NO synthetase interfering agents.

Refer to Kojima, H. et al., Anal. Chem., 1998, 70, 2446. for an example in which a reaction with NO was applied to an organic luminescent probe.

Advantages of the Invention

Although a PET mechanism has previously been used to control luminescence in ordinary organic compounds, a complex of the present invention offers a novel feature of being able to control a long life luminescence with about one million times longer lifetime compared to previous organic compounds by using a PET control on a lanthanide complex. Therefore, a time resolved luminescence measurement is made available which enables more precise measurement. Up to now, some examples of time resolved measurements using a lanthanide complex have been published, but no example in which the intensity of long life luminescence was controlled using a reaction with a target sample has been published. The present invention provides the first example in which a measurement of a long life luminescence according to a target sample becomes possible, and more extensive application is anticipated for the complex of the present invention.

The examples of the present invention below are provided to illustrate the present invention, but they are not provided with the intention of restricting the scope of the invention.

In the examples below, DTPA that forms a stable one to one complex with lanthanide ions ($Ln^{3+}$) was used as the chelate, and DTPA-cs124, a 2-quinolinol derivative, containing cs124 as a chromophore, represented by the formula (chemical formula 5) shown below,

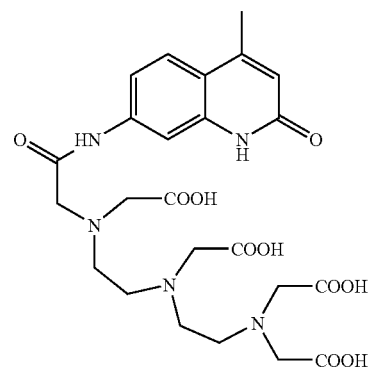

was used as the foundation skeleton. Then a lanthanide complex was designed and synthesized by incorporating a PET sensor to this skeleton. Aniline, which has a highly electron donating character, and acetanilide, which has a low electron donating nature, were selected as the PET sensors.

A PET sensor having a high electron donating characteristic did not emit luminescence since the electrons transferred to the chromophore. However, no electron transfer occurred from PET sensors having low electron donating character resulting in the emission of luminescence.

Figure 4:
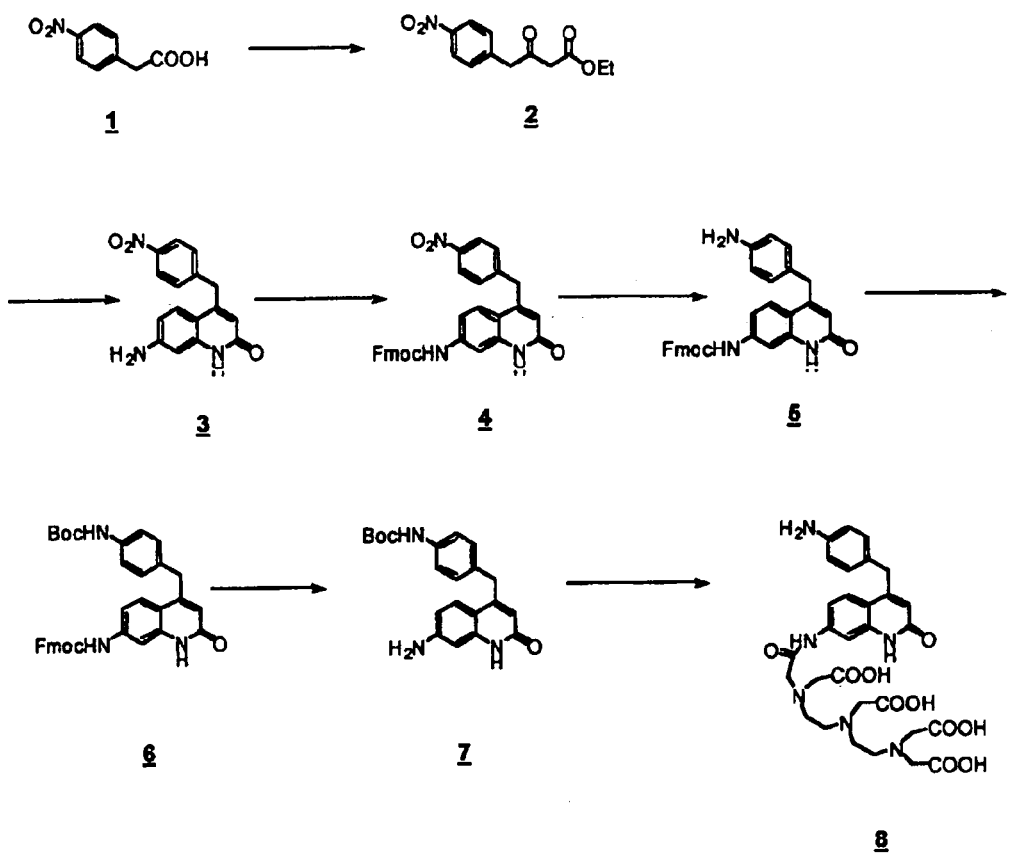
FIG. 4-6 show synthetic routes for the compounds 8, 11 and 15 prepared in Production Examples 1-3.
Figure 5:
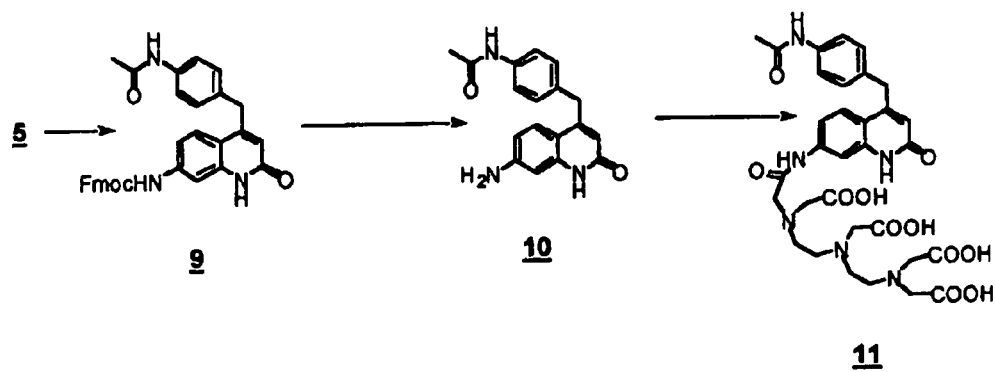
Figure 6:
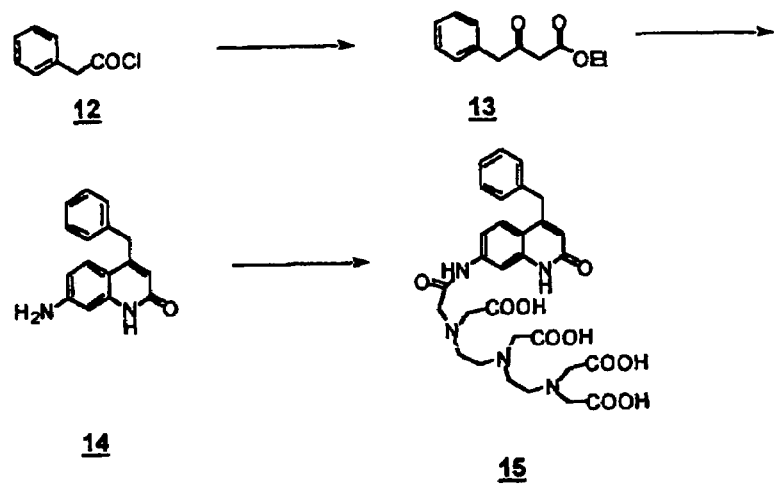
Figure 7:
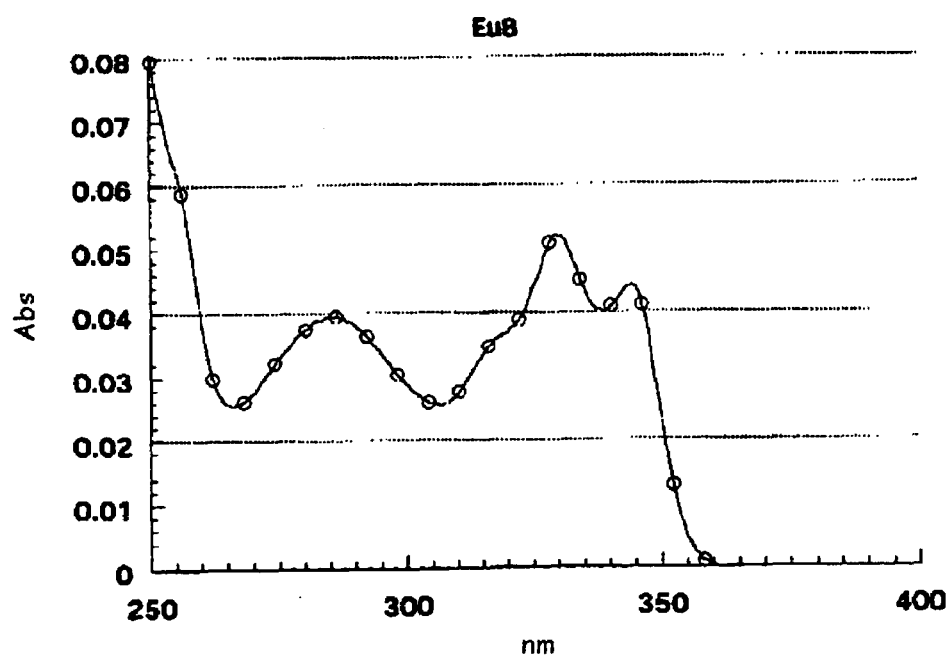
FIG. 7 shows an absorption spectrum of a europium (III) complex of DTPA-cs124.
Figure 8:
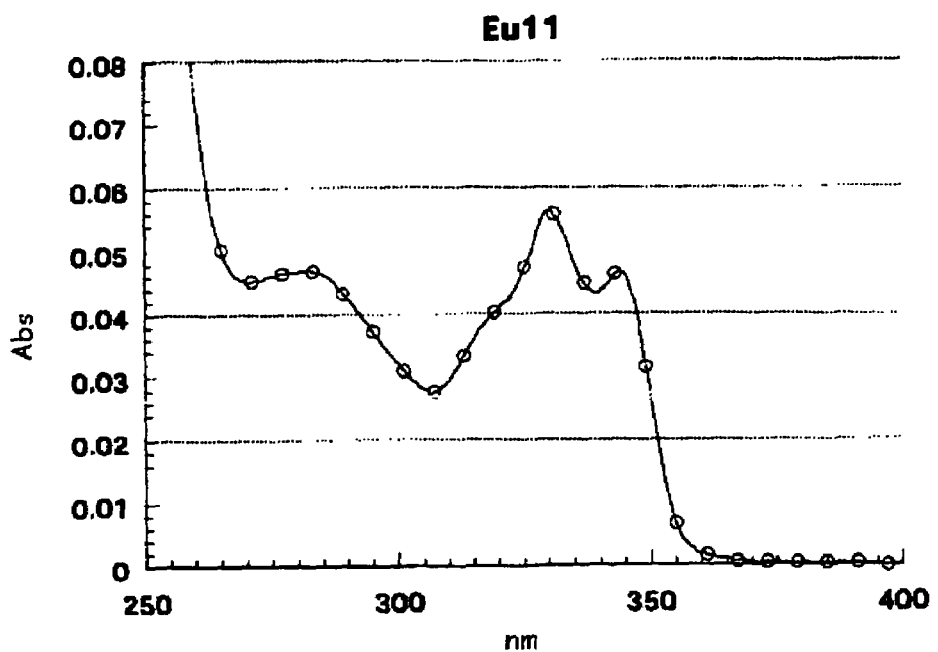
FIG. 8 shows an absorption spectrum of a europium (III) complex of Compound 8.
Figure 9:
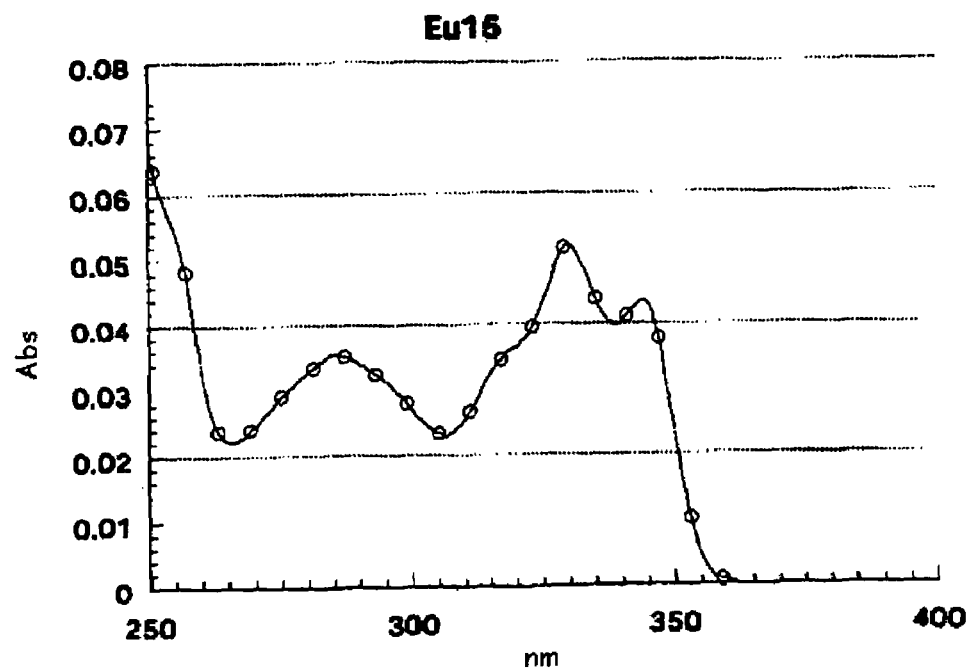
FIG. 9 shows an absorption spectrum of a europium (III) complex of Compound 11.
Figure 10:
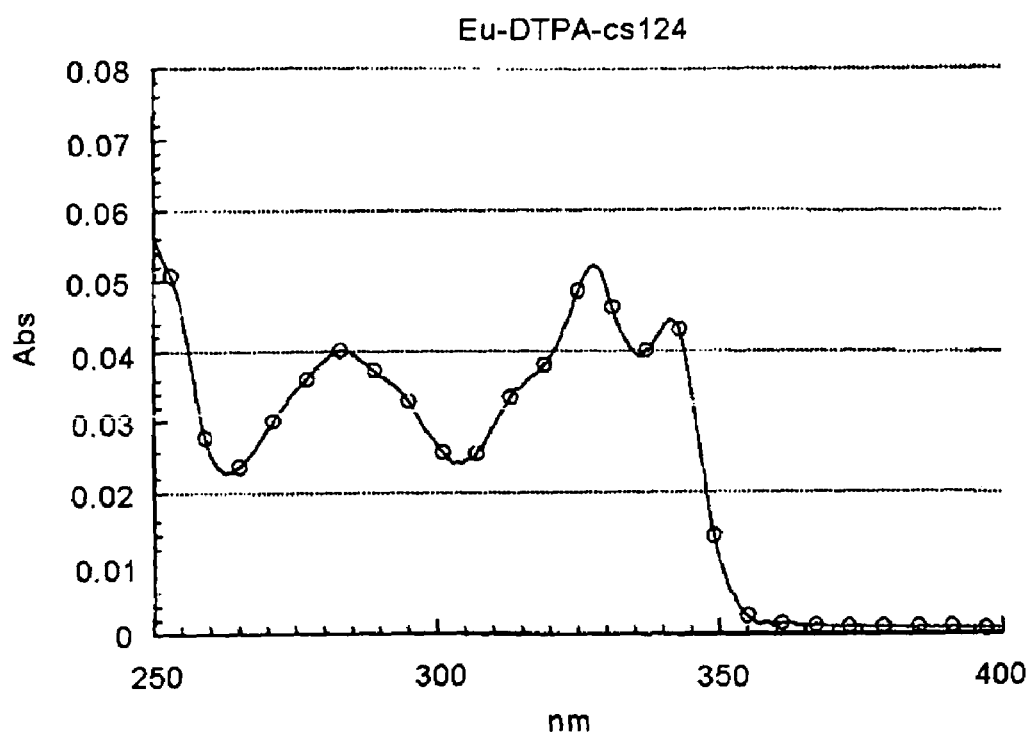
FIG. 10 shows an absorption spectrum of a europium (III) complex of Compound 15.

The individual compounds used in the Examples were synthesized and the synthetic routes are shown in FIGS. 4-6. Each compound number corresponds to the compound numbers in FIGS. 4-6.

PRODUCTION EXAMPLE 1

Compound 8 was synthesized in this production example.

20 ml of thionyl chloride and 20 ml of dichloromethane were used to dissolve 4,402 mg (24.3 mmoles) of 4-nitrophenyl acetic acid, and the solution was heated and refluxed for two hours. Thionyl chloride was distilled and removed under reduced pressure to obtain solids. The solids were dissolved in 30 ml of dichloromethane, and the solution was added dropwise over an hour while cooling with ice to 20 ml of a dichloromethane solution containing 3,499 mg (24.3 mmoles) of Meldrum's acid and 5,840 mg (49.8 mmoles) of N,N-diethyl isopropylamine, and the solution was agitated at room temperature for additional two hours. To this reaction solution was added 50 ml of 0.1N hydrochloric acid, and the solution was extracted using dichloromethane. This reaction solution was distilled under reduced pressure, and the solids obtained were dissolved in 100 ml of ethanol. The solution was heated and refluxed for two hours. This reaction solution was distilled under reduced pressure, and solids were obtained when the solution was left standing overnight at 4° C. The solids were recrystallized using ethanol, and 5,298 mg (21.1 mmoles) of Compound 2 was obtained. The product was in the form of yellow crystals, and the yield was 87%.

$^1$H-NMR (CDCl$_3$, 300 MHz): 1.29 (t, 3H, J=7.1), 3.52 (s, 2H), 4.00 (s, 2H), 4.21 (q, 2H, J=7.1), 7.41 (d, 2H, J=8.8), 8.21 (d, 2H, J=8.8), $^{13}$C-NMR (CDCl$_3$, 300 MHz): 14.1, 48.9, 49.0, 61.7, 123.8, 130.1, 130.5, 140.6, 166.8, 198.8.

MS (EI): 251

A mixture obtained by mixing 5,297 mg (21.1 mmoles) of Compound 2 and 2,290 mg (21.2 mmoles) of m-phenylene diamine was mixed and heated for twelve hours at 140° C. Methanol was added to the solids obtained, and the yellow solids that separated out were filtered using a Kiriyama funnel to obtain 1,876 mg (6.34 mmoles) of Compound 3. The yellow solids were obtained in 30% yield.

$^1$H-NMR (CDCl$_3$, 300 MHz): 4.15 (s, 2H), 5.75 (br, 2H), 5.91 (s, 1H), 6.35 (d, 1H, J=2.1), 6.39 (dd, 1H, J=8.4, 2.1). 7.34 (d, 1H, J=8.4), 7.55 (d, 2H, J=8.8), 8.15 (d, 2H, J=8.8), 11.24 (s, 1H).

$^{13}$C-NMR (DMSO-d$_6$, 75 MHz): 37.0, 96.8, 109.2, 110.6, 115.5, 123.6, 125.7, 129.9, 141.3, 146.1, 147.3, 149.2, 151.1, 162.3.

MS (FAB): 295.

A solution of 295 mg (1.0 mmole) of Compound 3, 297 mg (1.23 mmoles) of 9-fluorenylmethyloxycarbonyl chloride in 40 ml of dioxane and 20 ml of 0.5N aqueous sodium carbonate solution was agitated for twelve hours at room temperature. Water was added to the reaction solution, and the solids formed were filtered using a Kiriyama funnel. The solids were washed successively using methanol and water. The solids were recrystallized from ethanol, and 410 mg (0.79 mmole) of Compound 4 was obtained in the form of colorless crystals. The yield was 79%.

$^1$H-NMR (DMSO-d$_6$, 300 MHz) 4.29-4.33 (m, 3H), 4.48 (d, 2H, J=6.8), 6.20 (s, 1H, k), 7.12 (d, 1H, J=8.7), 7.31-7.44 (m, 4H), 7.55-7.62 (m, 3H), 7.66 (s, 1H), 7.74 (d, 2H, J=7.5), 7.89 (d, 2H, J=7.5), 8.17 (d, 2H, J=8.7), 10.02 (s, 1H), 11.65 (s, 1H)

$^{13}$C-NMR (DMSO-d$_6$, 75 MHz): 36.8, 46.5, 65.8, 103.6, 113.0, 113.9, 119.7, 120.2, 123.6, 125.1, 125.5, 127.1, 127.7, 130.0, 140.0, 140.8, 141.1, 143.7, 146.2, 146.8, 148.9, 153.2, 161.9.

MS (EI): 518.

40 ml of ethanol and 20 ml of acetic acid were used to dissolve 385 mg (0.74 mmole) of Compound 4 and 273 mg (4.96 mmoles) of iron powder, and the solution was heated and refluxed for two hours. The reaction solution was filtered using cerite, and the reaction solution was subsequently distilled under reduced pressure. The solids obtained were purified using silica gel chromatography to remove iron, and 200 mg of Compound 5 was obtained in the form of a mixture. Two hundred milligrams of this Compound 5 mixture was dissolved in 40 ml of dioxane and 20 ml of 0.5N aqueous sodium carbonate solution, and 300 μl of dibutyl carbonate was added to the reaction solution. The reaction mixture was agitated for twelve hours at room temperature. Water was added to this reaction solution, and the solution was extracted using ethyl acetate. The extractant solution was distilled under reduced pressure. The solids obtained were purified using silica gel chromatography, 111 mg (0.18 mmole) of Compound 6 was obtained. The solids were white, and the yield was 36% (two steps).

$^1$H-NMR (DMSO-d$_6$, 300 MHz): 1.52 (s, 9H), 4.09 (s, 2H), 4.38 (t, 1H, J=6.6), 4.55 (d, 2H, J=6.8), 6.15 (s, 1H), 7.17-7.23 (m, 3H), 7.39-7.51 (m, 6H), 7.68-7.71 (m, 2H), 7.82 (d, 2H, J=7.6), 7.97 (d, 2H, J=7.6), 9.34 (s, 1H), 10.07 (s, 1H), 11.64 (s, 1H)

$^{13}$C-NMR (DMSO-d$_6$, 75 MHz): 28.1, 36.7, 46.6, 65.8, 78.9, 103.6, 112.9, 114.1, 118.3, 119.0, 120.2, 125.2, 127.1, 127.7, 129.1, 131.7, 137.9, 140.0, 140.8, 140.9, 143.7, 150.5, 152.8, 153.3, 162.1.

MS (FAB): 588.

104 mg (0.18 mmole) of Compound 6 was dissolved in 10 ml of N,N-dimethylformamide, and 1 ml of piperidine was added, and the solution was agitated at room temperature for two hours. The reaction solution was distilled under reduced pressure, and the solids obtained were purified using silica gel chromatography to obtain 63 mg (0.17 mmole) of Compound 7. The solids were pale yellow, and the yield was 97%.

$^1$H-NMR (DMSO-d$_6$, 300 MHz): 1.39 (s, 9H), 3.87 (s, 2H), 5.66 (s, 2H), 5.74 (s, 1H), 6.28 (d, 1H, J=2.0), 6.32 (dd, 1H, J=9.6 2.0), 7.06 (d, 2H, J=8.4), 7.28-7.33 (m, 3H), 9.20 (s, 1H), 11.11 (s, 1H).

$^{13}$C-NMR (DMSO-d$_6$, 75 MHz): 28.1, 36.8, 78.9, 96.8, 109.4, 110.4, 114.9, 118.2, 125.7, 129.0, 132.2, 137.8, 141.1, 150.7, 150.9, 152.8, 162.4.

MS (FAB): 366.

44 mg (0.12 mmole) of anhydrous DTPA was dissolved in 10 ml of N,N-dimethylformamide and 400 microliters of triethylamine was added. Furthermore, 37 mg (0.10 mmole) of the compound dissolved in 10 ml of N,N-dimethylformamide was added dropwise to the reaction solution over 20 minutes. The reaction mixture was agitated for two hours at room temperature, 4 ml of water was added, and the reaction solution was distilled under reduced pressure. 5 ml of trifluoroacetic acid was added to the solids obtained, and the reaction mixture was agitated for an hour at room temperature. The reaction was distilled under reduced pressure, and the solids obtained were purified using high speed liquid chromatography to obtain 19 mg (0.03 mmole) of Compound 8. The solids were colorless, and the yield was 30%.

$^1$H-NMR (CD$_3$OD, 300 MHz): 3.05-3.30 (m, 4H), 3.35-3.60 (m, 12H), 4.19 (s, 2H,4.29 (s, 2H), 6.12 (s, 1H), 7.22-7.33 (m, 5H), 7.68 (d, 1H, J=7.9), 7.94 (s, 1H).

$^{13}$C-NMR (CD$_3$OD, 75 MHz):

MS (FAB): 641.

PRODUCTION EXAMPLE 2

Compound 11 was synthesized in this production example.

In the manner Compound 6 was synthesized in Production Example 1, 172 mg of Compound 5 was obtained in the form of a mixture from 209 mg (0.41 mmole) of Compound 4. The product was dissolved in 50 ml of acetic acid, and 10 ml of acetic anhydride was added. The reaction mixture was heated and refluxed for 30 minutes, and the reaction solution was distilled under reduced pressure. The solids obtained were purified using silica gel chromatography, and 169 mg (0.32 mmole) of Compound 9 was obtained. The solids were white, and the yield was 79%.

$^1$H-NMR (DMSO-d$_6$, 300 MHz): 2.00 (s, 3H), 3.95 (s, 2H), 5.71 (s, 2H), 5.81 (s, 1H), 6.34 (d, 1H, J=2.1), 6.39 (dd, 1H, J=8.6 2.1), 7.16 (d, 2H, J=8.4), 7.37 (d, 1H, J=8.6), 7.48 (d, 2H, J=8.4), 9.86 (s, 1H), 11.16 (s, 1H).

$^{13}$C-NMR (DMSO-d$_6$, 75 MHz): 171.3, 168.1, 162.1, 153.2, 150.3, 143.7, 140.9, 140.8, 140.0, 137.8, 132.8, 129.1, 127.7, 127.1, 125.5, 125.2, 120.2, 119.2, 114.1, 112.9, 103.6, 65.8, 46.6, 36.7, 24.0.

FABMS (M+1)

Using the same synthesis method used to obtain Compound 7, 94 mg (0.31 mmole) of Compound 10 was obtained from 167 mg (0.32 mmole) of Compound 9. The solids were pale yellow, and the yield was 97%.

$^1$H-NMR (DMSO-d$_6$, 300 MHz): 2.00 (s, 3H), 4.04 (s, 2H), 4.31 (t, 1H, J=6.9), 4.47 (d, 2H, J-6.9), 6.09 (s, 1H), 7.14 (d, 1H, J=8.4), 7.18 (d, 2H, J=8.7), 7.31-7.44 (m, 4H), 7.63 (d, 2H, J=8.7), 7.61-7.65 (m, 2H), 7.75 (d, 2H, J=7.6), 7.90 (d, 2H, J-7.5), 9.89 (s, 1H), 10.00 (s, 1H), 11.57 (s, 1H).
$^{13}$C-NMR (DMSO-d$_6$, 75 MHz): 168.1, 162.4, 150.9, 150.6, 141.1, 137.6, 133.2, 129.0, 125.7, 119.1, 114.9, 110.4, 109.4, 96.8, 36.8, 23.9.
FABMS (M+1) 683.

PRODUCTION EXAMPLE 3

Compound 15 was synthesized in this production example.

30 ml of dichloromethane was used to dissolve 2,319 mg (15.0 mmoles) of phenyl acetylchloride, Compound 12, and the solution was added dropwise over an hour while cooling with ice to 30 ml of dichloromethane used to dissolve 2,160 mg (14.9 mmoles) of Meldrum's acid and 3,877 mg (30.0 mmoles) of N,N-diethyl isopropylamine. This solution was further agitated at room temperature for two hours. 50 ml of 0.1N hydrochloric acid was added to this reaction solution, and the solution was extracted using dichloromethane. The reaction solution was distilled under reduced pressure, and the solids obtained were dissolved in 100 ml of ethanol. The solution was heated and refluxed for two hours. This reaction solution was distilled under reduced pressure to obtain 2,737 mg (13.3 mmoles) of Compound 12. The compound was pale yellow liquid, and the yield was 88%.

$^1$H-NMR (DMSO-d$_6$, 300 MHz): 1.16 (t, 3H, J=6.9), 3.64 (c, 2H), 3.85 (s, 2H), 4.06 (q, 2H, J=6.9), 7.00-7.41 (m, 5H).
$^{13}$C-NMR (CDCl$_3$, 75 MHz): 200.3, 166.9, 133.0, 129.3, 128.5, 127.0, 61.1, 49.7, 48.0, 13.8.
MS (EI): 251.

Using the same method used to synthesize Compound 3, 555 mg (2.22 mmoles) of Compound 14 was obtained from 1,200 mg (0.17 mmole) of Compound 13. The solids were pale yellow, and the yield was 38%.

$^1$H-NMR (DMSO-d$_6$, 300 MHz): 4.01 (s, 2H), 5.73 (s, 2H), 5.83 (s, 1H), 6.34 (d, 1H, J=2.1), 6.38 (dd, 1H, J=8.7 2.1), 7.17-7.32 (m, 5H), 7.41 (d, 2H, J=8.7), 11.18 (s, 1H).
$^{13}$C-NMR (DMSO-d$_6$, 75 MHz): 162.4, 151.0, 150.5, 141.2, 138.8, 128.8, 128.4, 126.3, 125.7, 115.1, 115.0, 110.4, 109.5, 96.9, 37.3.
FABMS (M+1): 251.

Using the same method used to synthesize Compound 11, 37 mg (0.06 mmole) of Compound 15 was obtained from 38 mg (0.15 mmole) of Compound 14. The solids were pale yellow, and the yield was 38%.

$^1$H-NMR (DMSO-d$_6$, 300 MHz): 3.05-3.30 (m, 4H), 3.35-3.60 (m, 12H), 4.13 (s, 2H), 4.35 (s, 2H), 6.18 (s, 1H), 7.12-7.23 (m, 6H), 7.68 (s, 1H), 7.96 (s, 1H).
$^{13}$C-NMR (CD$_3$OD, 75 MHz):
FABMS (M+1): 626.

In Examples below, Compounds 8, 11 and 15 obtained in Production Examples 1-3 were used to prepare complexes and their luminescent characteristics were evaluated.

EXAMPLES 1-3

Compounds 8, 11 and 15 each were dissolved in dimethyl sulfoxide to prepare 10 mM stock solutions. In addition, terbium (III) chloride hexahydrate was dissolved in dimethyl sulfoxide to prepare a 10 mM stock solution. Equal volumes of the terbium (III) chloride hexahydrate solution prepared were added to the individually prepared solutions of Compounds 8, 11 and 15, and, the resulting solutions were left standing for 30 minutes at room temperature to prepare terbium (III) complexes of Compounds 8, 11 and 15. The solutions were diluted using a 100 mM HEPES buffer (pH 7.4), and the luminescences of 8 μM solutions were measured.

EXAMPLES 4-6

Compounds 8, 11 and 15 each were dissolved in dimethylsulfoxide to prepare 10 mM stock solutions. In addition, europium (III) chloride hexahydrate was dissolved in dimethylsulfoxide to prepare a 10 mM stock solution. Equal volumes of the europium (III) chloride hexahydrate solution were added to the individually prepared solutions of Compounds 8, 11 and 15, and the resulting solutions were left standing for 30 minutes at room temperature to prepare the europium (III) complexes of the Compounds 8, 11 and 15. These solutions were diluted using 100 mM HEPES buffer solution (pH 7.4), and the luminescences of the 8 μM solutions were measured.

The absorption spectra of these europium (III) complexes and a europium (III) complex of DTPA-cs124 [5 μM in 100 mM HEPES buffer (pH 7.4)] are shown in FIGS. 7-10.

Luminescences were measured using a time resolved measurement. Luminescences were measured for all complexes at an excitation wavelength of 330 nm, a delay time of 0.05 ms and a gate time of 1.00 ms. In addition, the luminescence lifetimes were measured using an excitation wavelength of 33 nm, and the luminescence wavelengths were measured using 545 nm for individual terbium complexes and 615 nm for individual europium complexes [100 mM HEPES buffer (pH 7.4) in each 8 μM].

Figure 11:
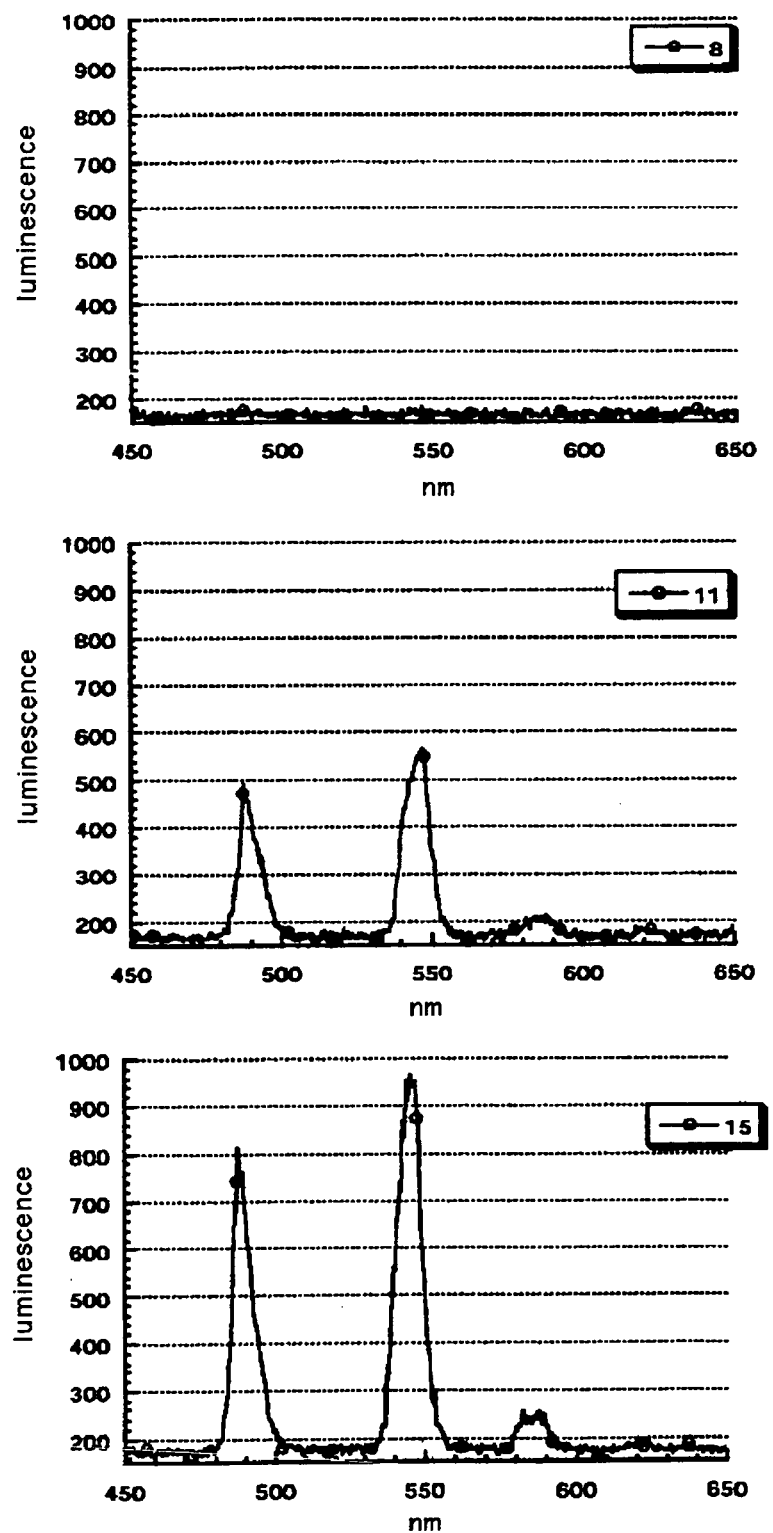
FIG. 11 shows luminescence spectra of terbium (III) complexes of the compounds 8 (top), 11 (middle) and 15 (bottom).

The luminescence spectra of the terbium (III) complexes of Compounds 8, 11 and 15 are shown in FIG. 11, and their luminescence life and water coordination numbers are shown in Table 1.

TABLE 1

|  | Life time (H$_2$O) | Life time (D$_2$O) | Water coordination number |
|---|---|---|---|
| DTPA-cs124 | 1.46 ms | 2.55 ms | 1.23 |
| (Tb11) | 1.17 ms | 1.81 ms | 1.27 |
| (Tb15) | 1.24 ms | 2.00 ms | 1.29 |

(Tb8) could not be measured.

Figure 12:
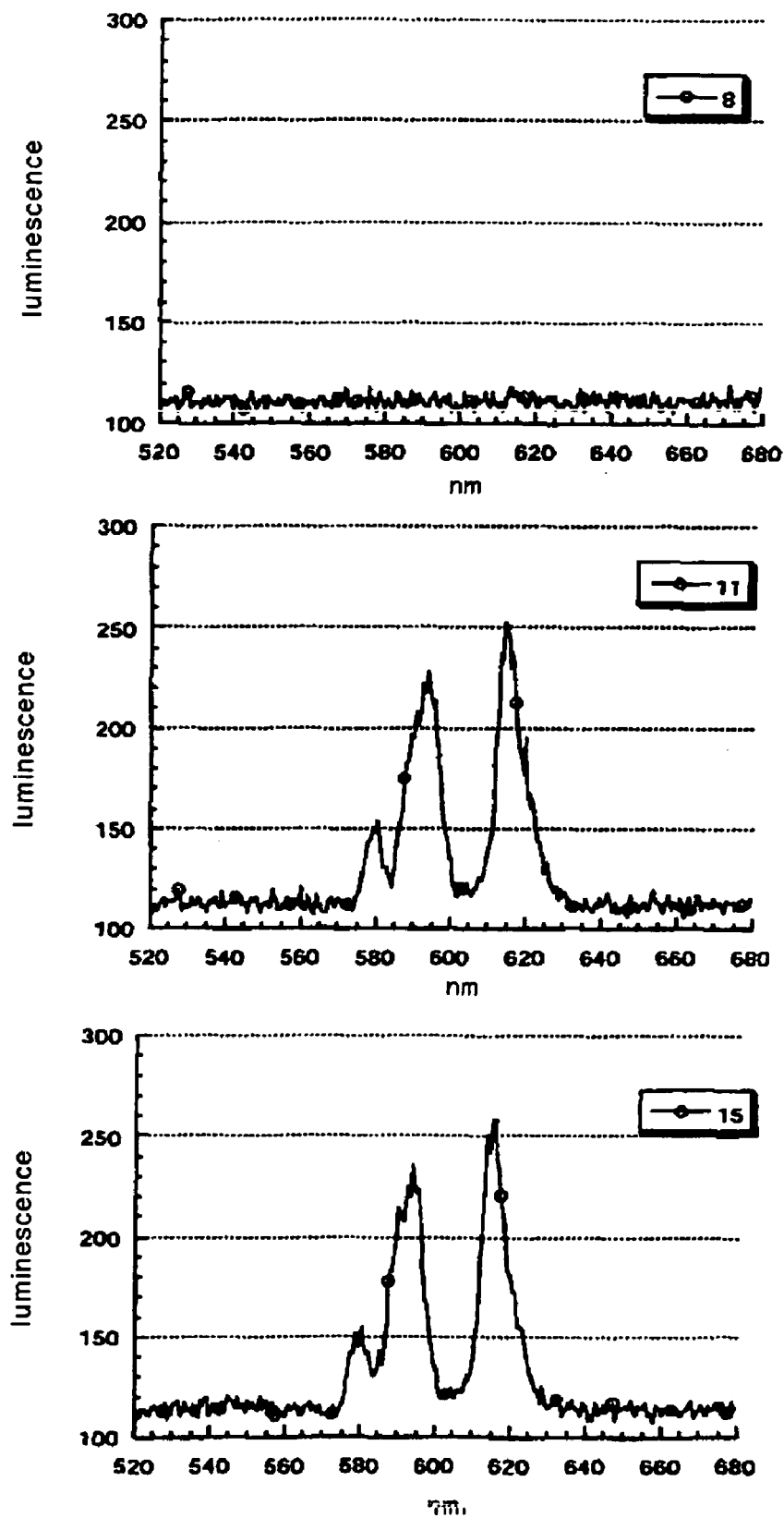
FIG. 12 shows luminescence spectra of europium (III) complexes of the compounds 8 (top), 11 (middle) and 15 (bottom).

In addition, the luminescence spectra of the europium (III) complexes of Compounds 8, 11 and 15 are shown in FIG. 12, and their luminescence life and water coordination numbers are shown in Table 2.

TABLE 2

| Europium complexes: Luminescence lives and water coordination numbers. | | | |
|---|---|---|---|
|  | Life time (H$_2$O) | Life time (D$_2$O) | Water coordination number |
| DTPA-cs124 | 0.59 ms | 2.38 ms | 1.34 |
| (Tb11) | 0.60 ms | 2.43 ms | 1.43 |
| (Tb15) | 0.61 ms | 2.42 ms | 1.29 |

(Eu8) could not be measured.

The terbium (III) complex and europium (III) complex of Compound 15 both emitted intense luminescence. The luminescence intensity of the terbium (III) complex and europium (III) complex of DTPA-cs124 was almost identical. In addition, no change was observed in their luminescence lives. The luminescence characteristics did not change when the 4 position in a carbostyryl segment was changed to a benzyl group.

The terbium (III) complex and europium (III) complex of Compound 11 both emitted intense luminescence. However, neither the terbium (III) complex nor the europium (III) complex of Compound 8 emitted luminescence at all, and their luminescence lifetimes could not be measured. Raising the electron density of the position 4 substituent in the carbostyryl segment caused a photo induced electron transfer from the position 4 substituent to the carbostyryl, and the terbium (III) complex and europium (III) complex of Compound 8 did not emit luminescence at all.

The data presented indicated that the luminescence in lanthanide complexes, including terbium (III) and europium (III) complexes could be controlled. Stable complexes in water were formed, the luminescence could be completely controlled and the complexes clearly functioned in water. The results indicated that a highly sensitive probe for a variety of analytical target materials could be developed by using an electron donating segment formed through a photo induced electron transfer and changing its electron donating capability to provide a sensor for the analytical target materials.

What is claimed is:

1. A luminescent lanthanide complex comprising a lanthanide and a substituted 2-quinolinol having a sensor group and a complex group on any two of the positions 3-8 in the 2-quinolinol represented by the formula

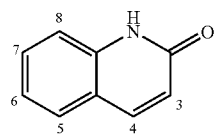

wherein the sensor group is represented by the formula

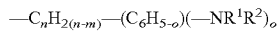

wherein n is an integer of 1-5, m is an integer of 0-2 and smaller than n-1, o is 1 or 2, $R^1$ represents H, alkyl, —COX (wherein X represents alkyl or peptide) or —CH$_2$CH$_2$(NYCH$_2$CH$_2$)$_p$NY$_2$ (wherein Y independently represents H, alykyl or a group having the formula

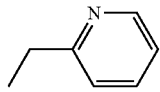

and p represents an integer of 0-3, and $R^2$ represents H or alkyl—), said lanthanide ion is complex bonded to said complex group, and the molar ratio of said substituted 2-quinolinol: said lanthanide is 1:0.9 to 1.1.

2. The luminescent lanthanide complex of claim 1 wherein said complex group is derived from any one of the chelates shown below and one of the N atoms in the chelate is bonded to said 2-quinolinol through —CH$_2$(CONH)$_q$—, wherein q represents 0 or 1,

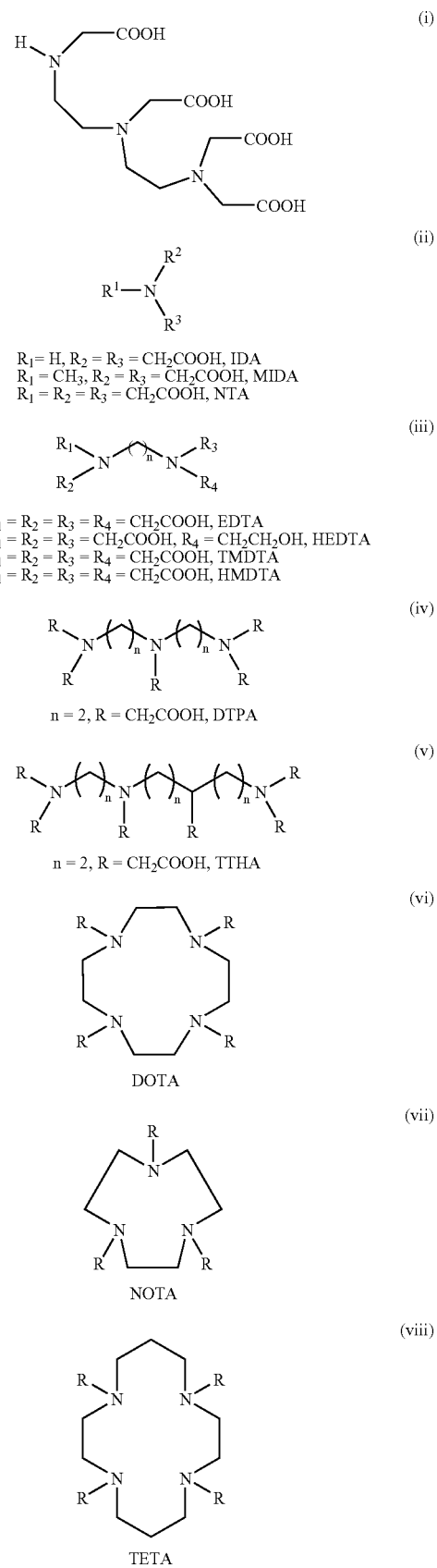

-continued (ix) 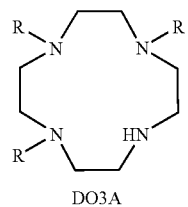

DO3A (x) 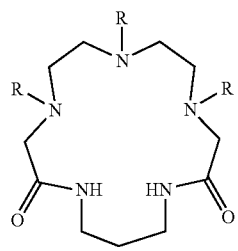

(xi) 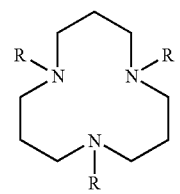

(xii) 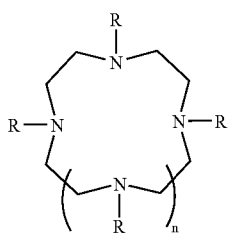

(xiii) 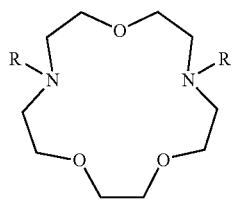

(xiv) 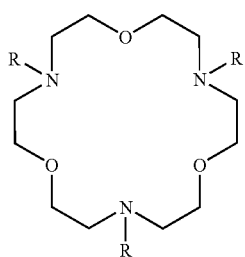

-continued (xv) 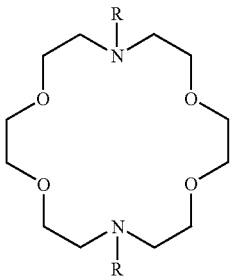

R = CH$_2$COOH ((vi)~(xv))

3. The luminescent lanthanide complex of claim 1 wherein said complex group is bonded to position 7 of said 2-quinolinol while said sensor group is bonded to position 4 or 3 of said 2-quinolinol, or said complex group is bonded to position 4 of said 2-quinolinol while said sensor group is bonded to position 3 or 7 of said 2-quinolinol, or said complex group is bonded to position 3 of said 2-quinolinol while said sensor group is bonded to position 4 or 7 of said 2-quinolinol.

4. The luminescent lanthanide complex of claim 1 wherein, in said sensor group, at least one amino group (—NR$^1$R$^2$) is positioned para to a divalent hydrocarbon group (—C$_n$H$_{2(n-m)}$—) on the benzene ring (C$_6$H$_{5-o}$), and the alikyl is methyl.

5. The luminescent lanthanide complex of claim 1 wherein n is 1 and m is 0.

6. A sensor comprising the luminescent lanthanide complex of claim 1.

7. A PET sensor comprising the luminescent lanthanide complex of claim 1.

8. The luminescent lanthanide complex of claim 2 wherein said complex group is bonded to position 7 of said 2-quinolinol while said sensor group is bonded to position 4 or 3 of said 2-quinolinol, or said complex group is bonded to position 4 of said 2-quinolinol while said sensor group is bonded to position 3 or 7 of said 2-quinolinol, or said complex group is bonded to position 3 of said 2-quinolinol while said sensor group is bonded to position 4 or 7 of said 2-quinolinol.

9. The luminescent lanthanide complex of claim 8 wherein, in said sensor group, at least one amino group (—NR$^1$R$^2$) is positioned para to a divalent hydrocarbon group (—C$_n$H$_{2(n-m)}$—) on the benzene ring (C$_6$H$_{5-o}$), and the alkyl is methyl.

10. The luminescent lanthanide complex of claim 9 wherein n is 1 and m is 0.

11. A sensor comprising the luminescent lanthanide complex of claim 9.

\* \* \* \* \*